United States Patent [19]

Haga et al.

[11] Patent Number: 4,619,687

[45] Date of Patent: Oct. 28, 1986

[54] TRIAZOLOPYRIDAZINES AND THEIR USE AS HERBICIDES

[75] Inventors: Toru Haga, Takarazuka; Eiki Nagano, Nishinomiya; Ryo Sato; Kouichi Morita, both of Toyonaka, all of Japan

[73] Assignee: Sumitomo Chemical Company, Limited, Osaka, Japan

[21] Appl. No.: 779,865

[22] Filed: Sep. 25, 1985

[30] Foreign Application Priority Data

Sep. 27, 1984 [JP] Japan .................................. 59-203785
Dec. 27, 1984 [JP] Japan .................................. 59-279449

[51] Int. Cl.$^4$ ..................... A01N 43/84; C07D 498/04
[52] U.S. Cl. .......................................... 71/92; 544/105
[58] Field of Search ............................. 544/105; 71/92

[56] References Cited

U.S. PATENT DOCUMENTS 3,770,734 11/1973 Pesson et al. ........................ 544/105

*Primary Examiner*—Richard L. Raymond
*Attorney, Agent, or Firm*—Birch, Stewart, Kolasch & Birch

[57] ABSTRACT

A compound of the formula:

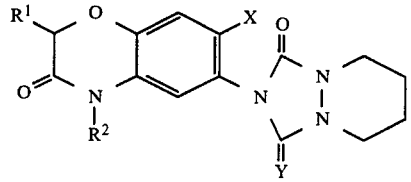

wherein $R^1$ is a hydrogen atom or a methyl group, $R^2$ is a $C_1$-$C_5$ alkyl group, a $C_3$-$C_4$ alkenyl group, a $C_3$-$C_4$ alkynyl group or a $C_1$-$C_4$ alkoxymethyl group, X is a hydrogen atom or a fluorine atom and Y is an oxygen atom or a sulfur atom, which is useful as a herbicide.

20 Claims, No Drawings

TRIAZOLOPYRIDAZINES AND THEIR USE AS HERBICIDES

This invention relates to triazolopyridazines, and their production and use. More particularly, it relates to triazolopyridazines of the formula:

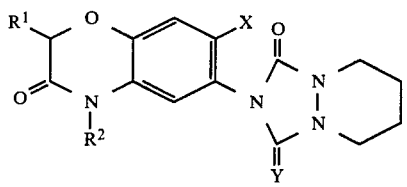

wherein $R^1$ is a hydrogen atom or a methyl group, $R^2$ is a $C_1$–$C_5$ alkyl group, a $C_3$–$C_4$ alkenyl group, a $C_3$–$C_4$ alkynyl group or a $C_1$–$C_4$ alkoxymethyl group, X is a hydrogen atom or a fluorine atom and Y is an oxygen atom or a sulfur atom, and their production and use.

It has been found that the triazolopyridazines (I) show a high herbicidal activity against a wide variety of weeds including broad-leaved weeds, Graminaceous weeds, Commelinaceous weeds and Cyperaceous weeds in agricultural plowed field by foliar or soil treatment without producing any material phytotoxicity on various agricultural crops such as corn, wheat, rice plant, soybean and cotton. Examples of broad-leaved weeds are wild buckwheat (*Polygonum convolvulus*), pale smartweed (*Polygonum lapthifolium*), common purslane (*Portulaca oleracea*), common chickweed (*Stellaria media*), common lambsquarters (*Chenopodium album*), redwood pigweed (*Amaranthus retroflexus*), radish (*Raphanus sativus*), wild mustard (*Sinapis arvensis*), hemp sesbania (*Sesbania exaltata*), sicklepod (*Cassia obtusifolia*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), jimsonweed (*Datura stramonium*), black nightshade (*Solanum nigrum*), persian speedwell (*Veronica persica*), common cocklebur (*Xanthium pensylvanicum*), common sunflower (*Helianthus annuus*), scentless chamomile (*Matricaria perforate*), corn marigold (*Chrysanthemum segetum*), etc. Examples of Graminaceous weeds are Japanese millet (*Echinochloa frumentacea*), barnyardgrass (*Echinochloa crus-galli*), green foxtail (*Setaria viridis*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), etc. Examples of Commelinaceous weeds are asiatic dayflower (*Commelina communis*), etc. Examples of Cyperaceous weeds are yellow nutsedge (*Cyperus esculentus*), etc.

The compounds of the invention are likewise effective in exterminating paddy field weeds including Graminaceous weeds such as barnyardgrass (*Echinochloa oryzicola*), broad-leaved weeds such as common falsepimpernel (*Lindernia procumbens*), indian toothcup (*Rotala indica*) and waterwort (*Elatine triandra*), Cyperaceous weeds such as hardstem bulrush (*Scirpus juncoides*) and needle spikerush (*Eleocharis acicularis*), monochoria (*Monochoria vaginalis*) and arrowhead (*Sagittaria pygmaea*), etc. without causing any phytotoxicity to rice plants on flood fallowing treatment.

Among the triazolopyridazines (I), those wherein X is a fluorine atom are preferred. More preferred are those wherein $R^1$ is a hydrogen atom or a methyl group and $R^2$ is a 2-propynyl group or a 2-propenyl group. Specific examples are 2-[4-(2-propynyl)-7-fluoro-2H-1,4-benzoxazin-3(4H)-on-6-yl]hexahydro-1H-[1,2,4]-triazolo[1,2-a]pyridazine-1,3-dione, 2-[4-(2-propynyl)-7-fluoro-2H-1,4-benzoxazin-3(4H)-on-6-yl]hexahydro-3-thioxo-1H-[1,2,4]-triazolo[1,2-a]pyridazin-1-one, 2-[4-(2-propenyl)-7-fluoro-2H-1,4-benzoxazin-3(4H)-on-6-yl]hexahydro-1H-[1,2,4]-triazolo[1,2-a]pyridazine-1,3-dione, 2-[4-(2-propenyl)-7-fluoro-2H-1,4-benzoxazin-3(4H)-on-6-yl]hexahydro-3-thioxo-1H-[1,2,4]-triazolo[1,2-a]-pyridazin-1-one, 2-[2-methyl-4-(2-propynyl)-7-fluoro-2H-1,4-benzoxazin-3(4H)-on-6-yl]hexahydro-1H-[1,2,4]-triazolo-[1,2-a]pyridazine-1,3-dione, etc.

The triazolopyridazines (I) of the invention are obtainable by ring-closure of a benzoxazine of the formula:

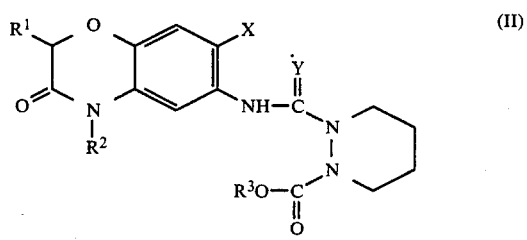

wherein $R^1$, $R^2$, X and Y are each as defined above and $R^3$ is a lower alkyl group, i.e. reacting the benzoxazine (II) with 0.01 to 1 equivalent amount of a base in a solvent at a temperature of 10° to 100° C. for a period of 10 minutes to 24 hours.

Examples of the solvent are aliphatic hydrocarbons (e.g. hexane, heptane, ligroin, petroleum ether), aromatic hydrocarbons (e.g. benzene, toluene, xylene), halogenated hydrocarbons (e.g. chloroform, carbon tetrachloride, dichloroethane, chlorobenzene, dichlorobenzene), ethers (e.g. diethyl ether, diisopropyl ether, dioxane, tetrahydrofuran, ethylene glycol dimethyl ether), ketones (e.g. acetone, methyl ethyl ketone, methyl isobutyl ketone, isophorone, cyclohexanone), alcohols (e.g. methanol, ethanol, isopropanol, t-butanol, octanol, cyclohexanol, methylcellosolve, diethylene glycol, glycerin), nitriles (e.g. acetonitrile, isobutyronitrile), tertiary amines (e.g. pyridine, triethylamine, N,N-diethylaniline, tributylamine, N-methylmorpholine), acid amides (e.g. formamide, N,N-dimethylformamide, N,N-dimethylacetamide), sulfur compounds (e.g. dimethylsulfoxide, sulfolane), and mixtures thereof.

As the base, there may be employed organic bases (e.g. pyridine, triethylamine, N,N-diethylaniline), inorganic bases (e.g. sodium hydroxide, potassium hydroxide, sodium carbonate, potassium carbonate, sodium hydride), alkali metal alkoxides (e.g. sodium methoxide, sodium ethoxide), etc.

After completion of the reaction, the reaction mixture is subjected to ordinary post-treatment. For instance, the reaction mixture is admixed with water, extracted with the solvent and concentrated. If necessary, the purification by chromatography or recrystallization may be applied.

Examples of the triazolopyridazines (I) obtainable by the above procedure are as shown in Table 1.

TABLE 1

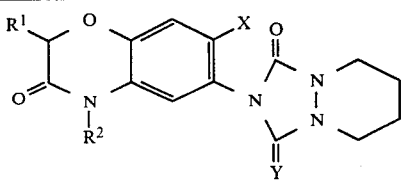

(I)

| R¹ | R² | X | Y |
|---|---|---|---|
| H | CH₃ | H | O |
| H | CH₃CH₂ | H | O |
| H | CH₃CH₂CH₂ | H | O |
| H | CH₃CH₂CH₂CH₂ | H | O |
| H | (CH₃)₂CHCH₂ | H | O |
| H | CH₃CH₂CH₂CH₂CH₂ | H | O |
| H | (CH₃)₂CHCH₂CH₂ | H | O |
| H | CH₃CH₂CHCH₂<br>       \|<br>       CH₃ | H | O |
| H | CH₂=C—CH₂ | H | O |
| H | CH₃CH=CHCH₂ | H | O |
| H | CH₂=C—CH₂<br>      \|<br>      CH₃ | H | O |
| H | CH≡C—CH₂ | H | O |
| H | CH₃C≡C—CH₂ | H | O |
| H | CH₃CH₂OCH₂ | H | O |
| CH₃ | CH₃CH₂ | H | O |
| CH₃ | CH₃CH₂CH₂ | H | O |
| CH₃ | CH₂=CH—CH₂ | H | O |
| CH₃ | CH≡C—CH₂ | H | O |
| H | CH₃ | F | O |
| H | CH₃CH₂ | F | O |
| H | CH₃CH₂CH₂ | F | O |
| H | (CH₃)₂CH | F | O |
| H | CH₃CH₂CH₂CH₂ | F | O |
| H | (CH₃)₂CHCH₂ | F | O |
| H | (CH₃)₂CHCH₂CH₂ | F | O |
| H | CH₃CH₂CHCH₂<br>       \|<br>       CH₃ | F | O |
| H | CH₃CH₂CH₂CH₂CH₂ | F | O |
| H | CH₂=CH—CH₂ | F | O |
| H | CH₃CH=CHCH₂ | F | O |
| H | CH₂=C—CH₂<br>      \|<br>      CH₃ | F | O |
| H | CH₃CH₂OCH₂ | F | O |
| H | CH≡C—CH₂ | F | O |
| H | CH₃C≡C—CH₂ | F | O |
| CH₃ | CH₃CH₂ | F | O |
| CH₃ | CH₃CH₂CH₂ | F | O |
| CH₃ | (CH₃)₂CHCH₂ | F | O |
| CH₃ | CH₂=CH—CH₂ | F | O |
| CH₃ | CH₃—CH=CH—CH₂ | F | O |
| CH₃ | CH₂=C—CH₂<br>      \|<br>      CH₃ | F | O |
| CH₃ | CH≡C—CH₂ | F | O |
| CH₃ | CH₃—C≡C—CH₂ | F | O |
| H | CH₃ | H | S |
| H | CH₃CH₂ | H | S |
| H | CH₃CH₂CH₂ | H | S |
| H | CH₃CH₂CH₂CH₂ | H | S |
| H | (CH₃)₃C—CH₂ | H | S |
| H | H₂C=CH—CH₂ | H | S |
| H | CH₃CH=CH—CH₂ | H | S |
| H | HC≡C—CH₂ | H | S |
| H | CH₃—C≡C—CH₂ | H | S |

TABLE 1-continued

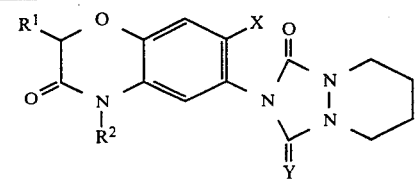

(I)

| R¹ | R² | X | Y |
|---|---|---|---|
| H | CH₃OCH₂ | H | S |
| H | CH₃CH₂OCH₂ | H | S |
| H | CH₃CH₂CH₂OCH₂ | H | S |
| CH₃ | CH₃CH₂ | H | S |
| CH₃ | CH₃CH₂CH₂ | H | S |
| CH₃ | H₂C=CH—CH₂ | H | S |
| CH₃ | HC≡C—CH₂ | H | S |
| CH₃ | CH₃CH₂OCH₂ | H | S |
| H | CH₃ | F | S |
| H | CH₃CH₂ | F | S |
| H | CH₃CH₂CH₂ | F | S |
| H | CH₃CH₂CH₂CH₂ | F | S |
| H | (CH₃)₂CHCH₂ | F | S |
| H | H₂C=CH—CH₂ | F | S |
| H | CH₃CH=CH—CH₂ | F | S |
| H | HC≡C—CH₂ | F | S |
| H | CH₃C≡C—CH₂ | F | S |
| H | CH₃OCH₂ | F | S |
| H | CH₃CH₂OCH₂ | F | S |
| H | CH₃CH₂CH₂OCH₂ | F | S |
| CH₃ | CH₃CH₂ | F | S |
| CH₃ | CH₃CH₂CH₂ | F | S |
| CH₃ | H₂C=CH—CH₂ | F | S |
| CH₃ | HC≡C—CH₂ | F | S |
| CH₃ | CH₃CH₂OCH₂ | F | S |

Practical and presently preferred embodiments for production of the triazolopyridazines (I) are illustratively shown in the following Examples.

EXAMPLE 1

1-[4-(2-Propynyl)-7-fluoro-2H-1,4-benzoxadin-3(4H)-on-6-ylaminocarbonyl]-2-ethoxycarbonylhexahydropyridazine (1.8 g) was added to methanol (30 ml), and after addition of a catalytic amount of sodium methoxide, the resultant mixture was heated under reflux for 2 hours. Water was added thereto, and the reaction mixture was extracted with ethyl acetate. The extract was washed with water, dried and concentrated to give crystals, which were washed with ether to give 2-[4-(2-propynyl)-7-fluoro-2H-1,4-benzoxadin-3(4H)-on-6-yl]hexahydro-1H-[1,2,4]triazolo[1,2-a]pyridazine-1,3-dione (1.1 g). m.p., 229°–231° C.

EXAMPLE 2

1-[4-(2-Propenyl)-7-fluoro-2H-1,4-benzoxadin-3(4H)-on-6-yliaminothiocarbonyl]-2-ethoxycarbonylhexahydropyridazine (0.7 g) was added to methanol (1.8 ml), and after addition of a catalytic amount of sodium methoxide, the resultant mixture was heated under reflux for 1.5 hours. Water was added thereto, and the reaction mixture was extracted with ethyl acetate. The extract was washed with water, dried and concentrated. The residue was purified by silica gel chromatography using a mixture of ethyl acetate and hexane (2:3) as an eluent to give 2-[4-(2-propenyl)-7-fluoro-2H-1,4-benzoxadin-3(4H)-on-6-yl]hexahydro-3-thioxo-1H-[1,2,4-triazolo[1,2-a]pyridazin-1-one (0.15 g). m.p., 218°–219° C.

In the same manner as above, the triazolopyridazines (I) as shown in Table 2 were obtained:

TABLE 2

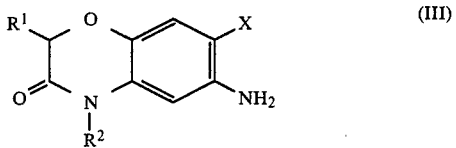

| Compound No. | R¹ | R² | X | Y | Physical constant |
|---|---|---|---|---|---|
| 1 | H | CH₃CH₃ | H | O | m.p. 172–173.5° C. |
| 2 | H | CH₃CH₂CH₂ | H | O | m.p. 152–153.5° C. |
| 3 | H | CH₂=CHCH₂ | H | O | m.p. 208–210° C. |
| 4 | H | CH≡CCH₂ | H | O | m.p. 221–223° C. |
| 5 | H | CH₃CH₂OCH₂ | H | O | m.p. 168–169° C. |
| 6 | CH₃ | CH≡CCH₂ | H | O | m.p. 188–189° C. |
| 7 | H | CH≡CCH₂ | F | O | m.p. 229–231° C. |
| 8 | CH₃ | CH₃CH₂CH₂ | F | O | m.p. 211–212° C. |
| 9 | CH₃ | CH₂=CHCH₂ | F | O | m.p. 160–161° C. |
| 10 | H | CH₃CH₂CH₂ | H | S | m.p. 225–226° C. |
| 11 | H | C₂H₅OCH₂ | H | S | m.p. 215–216° C. |
| 12 | H | H₂C=CHCH₂ | H | S | m.p. 218–219° C. |
| 13 | H | HC≡CCH₂ | H | S | m.p. 248–250° C. |
| 14 | CH₃ | HC≡CCH₂ | H | S | m.p. 265–268° C. |
| 15 | H | CH₃CH₂ | F | S | m.p. 212–213.5° C. |
| 16 | H | CH₃CH₂CH₂ | F | S | m.p. 167–168° C. |
| 17 | H | CH₃CH₂OCH₂ | F | S | m.p. 219–220.5° C. |
| 18 | H | H₂C=CHCH₂ | F | S | Glassy |
| 19 | H | HC≡CCH₂ | F | S | m.p. 265–266° C. |

The starting benzoxazines (II) are obtainable by reacting an aminobenzoxazine of the formula:

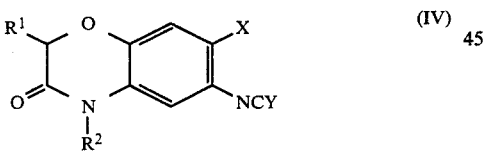

wherein R¹, R² and X are each as defined above with phosgene or thiophosgene by a per se conventional procedure [R. L. Shriner et al., Org.Synth.Coll. Vol., 2, 453 (1966)] to give an iso(thio)cyanate of the formula:

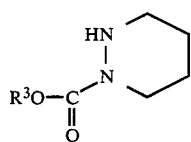

wherein R¹, R², X and Y are each as defined above, followed by reacting the resultant iso(thio)cyanate (IV) with a hexahydropyridazinecarboxylate of the formula:

(V)

$$\text{R}^3\text{O}-\overset{\text{O}}{\underset{\|}{\text{C}}}-\text{N}\overset{\text{HN}}{\diagdown}$$

wherein R³ is as defined above in a solvent in the presence of a base at a temperature of 0° to 100° C. for a period of 1 to 48 hours.

In the above reaction, the hexahydropyridazinecarboxylate (V) and the base are used respectively in a 1.0 to 1.1 equivalent amount and a catalytic amount to a 1.1 equivalent amount to one equivalent amount of the iso(thio)cyanate (IV). As the solvent, there may be used aromatic hydrocarbons (e.g. toluene, benzene), esters (e.g. ethyl acetate), halogenated hydrocarbons (e.g. chloroform), ethers (e.g. dioxane, dimethoxyethane), etc. Examples of the base are triethylamine, pyridine, N,N-dimethylaniline, N,N-diethylaniline, etc.

After completion of the reaction, the reaction mixture is subjected to ordinary post-treatment such as addition of water, extraction with an organic solvent and concentration. If desired, any conventional purification procedure such as recrystallization or chromatography may be adopted.

Said aminobenzoxazine (III) may be prepared, for instance, according to the following scheme:

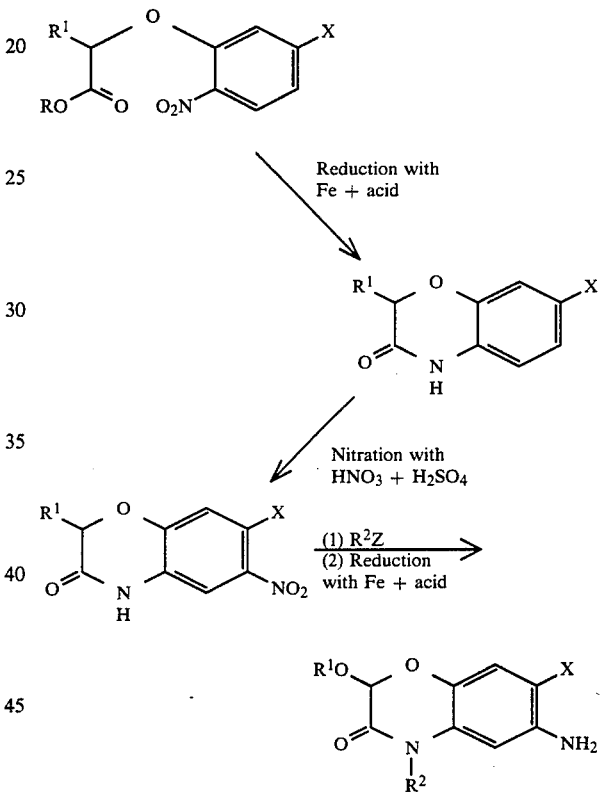

wherein R is a lower alkyl group, Z is a halogen atom and R¹, R² and X are each as defined above.

The aminobenzoxazine (III) may be also prepared according to the following scheme:

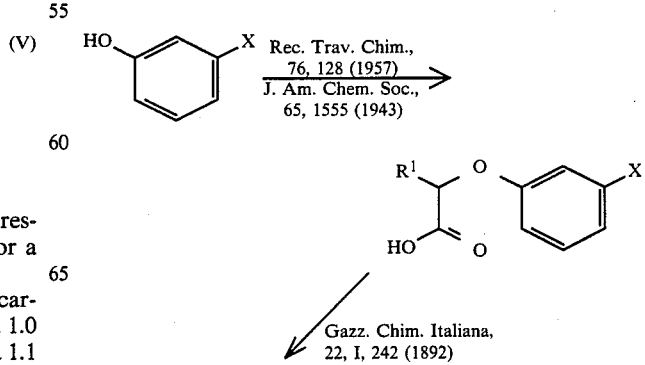

-continued

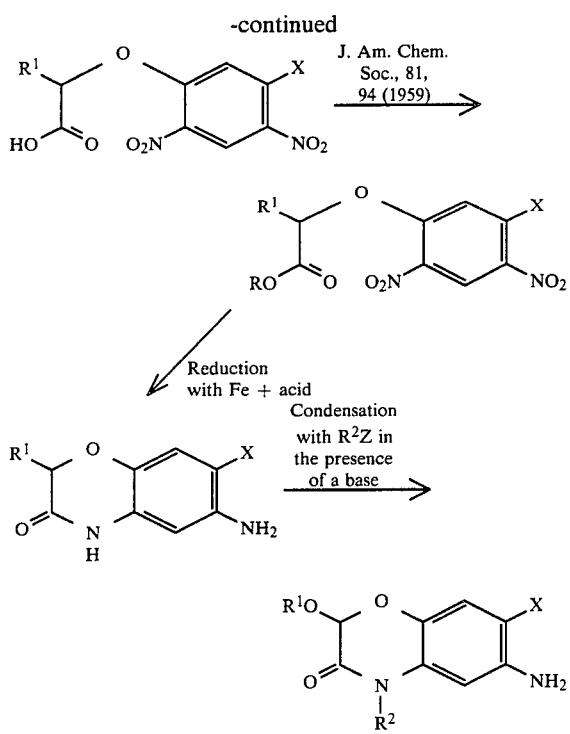

wherein R, $R^1$, $R^2$, X and Z are each as defined above.

On the practical usage of the triazolopyridazines (I), they may be formulated in any formulation form such as emulsifiable concentrates, wettable powders, suspensions, granules, etc. in combination with conventional solid or liquid carriers or diluents as well as surface active agents or auxiliary agents. The content of the triazolopyridazines (I) as the active ingredient in such preparation form is usually with a range of 0.03 to 90% by weight, preferably of 0.05 to 80% by weight.

Examples of the solid carrier or diluent are fine powders or granules of kaolin clay, attapulgite clay, bentonite, terra alba, pyrophyllite, talc, diatomaceous earth, calcite, walnut powders, urea, ammonium sulfate and synthetic hydrous silicate, etc. As the liquid carrier or diluent, there may be exemplified aromatic hydrocarbons (e.g. xylene, methylnaphthalene), alcohols (e.g. isopropanol, ethylene glycol, cellosolve), ketones (e.g. acetone, cyclohexanone, isophorone), soybean oil, cotton seed oil, dimethylsulfoxide, N,N-dimethylformamide, acetonitrile, water, etc.

The surface active agent used for emulsification, dispersion or spreading may be any of the anionic and non-ionic type of agents. Examples of the surface active agent include alkylsulfates, alkylarylsulfonates, dialkylsulfosuccinates, phosphates of polyoxyethylenealkylaryl ethers, polyoxyethylene alkyl ethers, polyoxyethylene alkylaryl ethers, polyoxyethylene polyoxypropylene block copolymer, sorbitan fatty acid esters, polyoxyethylene sorbitan fatty acid esters, etc. Examples of the auxiliary agents include ligninsulfonates, sodium alginate, polyvinyl alcohol, gum arabic, CMC (carboxymethyl cellulose), PAP (isopropyl acid phosphate), etc.

Practical embodiments of the herbicidal composition according to the invention are illustratively shown in the following examples wherein parts are by weight. The compound number of the active ingredient corresponds to the one in Table 2.

FORMULATION EXAMPLE 1

Fifty parts of Compound No. 4 or 18, 3 parts of calcium ligninsulfonate, 2 parts of sodium laurylsulfate and 45 parts of synthetic hydrous silicate are well mixed while being powdered to obtain a wettable powder.

FORMULATION EXAMPLE 2

Five parts of Compound No. 3 or 13, 14 parts of polyoxyethylenestyrylphenyl ether, 6 parts of calcium dodecylbenzenesulfonate, 30 parts of xylene and 45 parts of N,N-dimethylformamide are well mixed to obtain an emulsifiable concentrate.

FORMULATION EXAMPLE 3

Two parts of Compound No. 6 or 11, 1 part of synthetic hydrous silicate, 2 parts of calcium lignin-sulfonate, 30 parts of bentonite and 65 parts of kaolin clay are well mixed while being powdered. The mixture is then kneaded with water, granulated and dried to obtain granules.

FORMULATION EXAMPLE 4

Twenty-five parts of Compound No. 7 or 15 is mixed with 3 parts of polyoxyethylene sorbitan monooleate, 3 parts of carboxymethyl cellulose and 69 parts of water and pulverized until the particle size of the mixture becomes less than 5 microns to obtain a suspension.

The triazolopyridazines (I) thus formulated in any suitable formulation form are useful for the pre-emergence or post-emergence control of undesired weeds by soil or foliar treatment as well as flood fallowing treatment. These treatments include the application to the soil surface prior to or after the transplanting or the incorporation into the soil. The foliar treatment may be effected by spraying the herbicidal composition containing the triazolopyridazines (I) over the top of the plants. It may also be applied directly to the weeds if care is taken to keep the chemical off the crop foliage.

The triazolopyridazines (I) of the invention may be used together with other herbicides to improve their activity as herbicides, and in some cases, a synergistic effect can be expected. Further, they may be applied in combination with insecticides, acaricides, nematocides, fungicides, plant growth regulators, fertilizers, soil improvers, etc.

Furthermore, the triazolopyridazines (I) can be used as herbicides applicable to agricultural plowed field as well as paddy field. They are also useful as herbicides to be employed for orchard, pasture land, lawn, forest, nonagricultural field, etc.

The dosage rate of the triazolopyridazines (I) may vary on prevailing weather conditions, formulation used, prevailing season, mode of application, soil involved, crop and weed species, etc. Generally, however, the dosage rate is from 0.01 to 100 grams, preferably from 0.03 to 50 grams, of the active ingredient per are. The herbicidal composition of the invention formulated in the form of an emulsifiable concentrate, a wettable powder or a suspension may ordinarily be employed by diluting it with water at a volume of 1 to 10 liters per are, if necessary, with addition of an auxiliary agent such as a spreading agent. Examples of the spreading agent include, in addition to the surface active agents as noted above, polyoxyethylene resin acid (ester), ligninsulfonate, abietylenic acid salt, dinaphthylmethanedisulfonate, paraffin, etc. The composition formulated in the form of granules may be normally applied as such without dilution.

The biological data of the triazolopyridazines (I) as herbicides will be illustratively shown in the following Examples wherein the phytotoxicity to crop plants and the herbicidal activity on weeds were observed visually as to the degree of germination as well as the growth inhibition and rated with an index 0, 1, 2, 3, 4 or 5, in which the numeral "0" indicates no material difference is seen in comparison with the untreated plant and the numeral "5" indicates the complete inhibition or death of the test plants.

The compound shown in Table 3 below was used for comparison.

TABLE 3

| Compound No. | Chemical structure | Remarks |
|---|---|---|
| A | 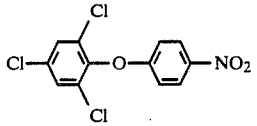 | Commercially available herbicide; "chloronitrofen" |

TEST EXAMPLE 1

Cylindrical plastic pots (diameter, 10 cm; height, 10 cm) were filled with upland field soil, and the seeds of Japanese millet, tall morningglory and velvetleaf were sowed therein and covered with soil. A designed amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 4.

TABLE 4

| Compound No. | Dosage (g/are) | Herbicidal activity | | |
|---|---|---|---|---|
| | | Japanese millet | Tall morningglory | Velvetleaf |
| 1 | 20 | 5 | 5 | 5 |
| 2 | 20 | 5 | 5 | 5 |
| 3 | 10 | 5 | 5 | 5 |
| 4 | 5 | 5 | 5 | 5 |
| 5 | 20 | 5 | 5 | 5 |
| 6 | 10 | 5 | 5 | 5 |
| 7 | 5 | 5 | 5 | 5 |
| 8 | 20 | 5 | 5 | 5 |
| 9 | 10 | 5 | 5 | 5 |
| 10 | 20 | 5 | 5 | 5 |
| 11 | 10 | 5 | 5 | 5 |
| 12 | 10 | 5 | 5 | 5 |
| 13 | 10 | 5 | 5 | 5 |
| 14 | 20 | 5 | 5 | 5 |
| 15 | 10 | 5 | 5 | 5 |
| 16 | 10 | 5 | 5 | 5 |
| 17 | 10 | 5 | 5 | 5 |
| 18 | 10 | 5 | 5 | 5 |
| 19 | 10 | 5 | 5 | 5 |
| A | 20 | 1 | 1 | 2 |
| | 10 | 0 | 0 | 0 |

TEST EXAMPLE 2

Cylindrical plastic pots (diameter, 10 cm; height, 10 cm) were filled with upland field soil, and the seeds of Japanese millet, radish and velvetleaf were sowed therein and cultivated in a greenhouse for 10 days. A designed amount of the test compound formulated in an emulsifiable concentrate according to Formulation Example 2 was diluted with water containing a spreading agent, and the dilution was sprayed over the foliage of the test plants by means of a small hand sprayer at a spray volume of 10 liters per are. The test plants were further grown in the greenhouse for 20 days, and the herbicidal activity was examined. The results are shown in Table 5.

TABLE 5

| Compound No. | Dosage (g/are) | Herbicidal activity | | |
|---|---|---|---|---|
| | | Japanese millet | Radish | Velvetleaf |
| 1 | 5 | — | 5 | 5 |
| 2 | 5 | 4 | 5 | 5 |
| 3 | 5 | 4 | 5 | 5 |
| 4 | 5 | 5 | 5 | 5 |
| | 2.5 | — | 5 | 5 |
| 6 | 5 | 4 | 5 | 5 |
| 7 | 5 | 5 | 5 | 5 |
| | 2.5 | — | 5 | 5 |
| 8 | 5 | 4 | 5 | 5 |
| 9 | 5 | 4 | 5 | 5 |
| 10 | 5 | 4 | 5 | 5 |
| 11 | 5 | 4 | 5 | 5 |
| 12 | 5 | 5 | 5 | 5 |
| | 2.5 | — | 5 | 5 |
| 13 | 5 | 5 | 5 | 5 |
| | 2.5 | — | 5 | 5 |
| 14 | 5 | 4 | 5 | 5 |
| 15 | 5 | 5 | 5 | 5 |
| 16 | 5 | 5 | 5 | 5 |
| 17 | 5 | 4 | 5 | 5 |
| 18 | 5 | 5 | 5 | 5 |
| 19 | 5 | 5 | 5 | 5 |
| | 2.5 | — | 5 | 5 |
| A | 5 | 2 | 0 | 3 |
| | 2.5 | — | 0 | 1 |

TEST EXAMPLE 3

Cylindrical plastic pots (diameter, 8 cm; height, 12 cm) were filled with paddy field soil, and the seeds of barnyardgrass (*Echinochloa oryzicola*), broad-leaved weeds (e.g. common falsepimpernel, indian toothcup, waterwort) and hardstem bulrush were sowed in 1 to 2 cm depth. Water was poured therein to make a flooded condition, and tubers of arrowhead were transplanted therein in 1 to 2 cm depth and grown in a greenhouse. Six days (at that time the weeds began to germinate) thereafter, a designed amount of the test compound formulated in an emulsifiable concentrate according to Formulation Example 2 and diluted with water (5 ml) was applied to the pots by perfusion. The test plants were grown for further 20 days in the greenhouse, and the herbicidal activity was examined. The results are shown in Table 6.

TABLE 6

| Compound No. | Dosage (g/are) | Herbicidal activity | | | |
|---|---|---|---|---|---|
| | | Barnyardgrass | Broad-leaved weed | Hardstem bulrush | Arrowhead |
| 1 | 10 | 5 | 5 | 4 | 5 |
| 2 | 10 | 5 | 5 | 4 | 5 |
| 3 | 10 | 5 | 5 | 5 | 5 |
| 4 | 10 | 5 | 5 | 5 | 5 |
| 5 | 20 | 5 | 5 | 5 | 5 |
| 6 | 10 | 5 | 5 | 5 | 5 |
| 7 | 10 | 5 | 5 | 5 | 5 |
| 8 | 10 | 5 | 5 | 4 | 5 |
| 9 | 10 | 5 | 5 | 5 | 5 |
| 11 | 20 | 5 | 5 | 5 | 5 |
| 13 | 20 | 5 | 5 | 5 | 5 |
| 14 | 20 | 5 | 5 | 5 | 5 |

TABLE 6-continued

| Compound No. | Dosage (g/are) | Barnyardgrass | Broad-leaved weed | Hardstem bulrush | Arrowhead |
|---|---|---|---|---|---|
| 15 | 20 | 5 | 5 | 5 | 5 |
| 19 | 20 | 5 | 5 | 5 | 5 |
| A | 20 | 5 | 5 | 4 | 4 |
|    | 10 | 4 | 5 | 2 | 2 |

TEST EXAMPLE 4

Vats (33 cm×23 cm×11 cm) were filled with upland field soil, and the seeds of soybean, corn, common cocklebur, tall morningglory, velvetleaf, redroot pigweed, black nightshade, hemp sesbania, green foxtail and large crabgrass were sowed therein to 1 to 2 cm depth. A designed amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 20 days, and the herbicidal activity was examined. The results are shown in Table 7.

TABLE 7

| Compound No. | Dosage (g/are) | Soybean | Corn | Common cocklebur | Tall morningglory | Velvetleaf | Redroot pigweed | Black nightshade | Hemp sesbania | Green foxtail | Large crabgrass |
|---|---|---|---|---|---|---|---|---|---|---|---|
| 1 | 2.5 | — | — | 5 | 5 | 5 | 5 | 5 | 5 | 5 | 5 |
|   | 1.25 | — | 1 | 4 | 5 | 5 | 5 | 5 | 5 | 4 | — |
| 2 | 2.5 | 2 | 2 | 5 | 4 | 5 | 5 | 5 | 5 | 4 | 4 |
|   | 1.25 | 0 | 0 | 4 | — | 5 | 5 | 4 | 4 | — | — |
| 3 | 1.25 | — | — | 5 | 5 | 5 | 5 | 5 | 5 | 4 | 4 |
|   | 0.63 | 1 | 1 | 4 | 4 | — | 5 | 4 | — | — | — |
| 4 | 1.25 | — | — | 5 | 5 | 5 | 5 | 5 | 5 | 5 | 5 |
|   | 0.63 | — | 1 | 5 | 4 | 5 | 5 | 5 | 5 | — | — |
| 7 | 1.25 | — | — | 5 | 5 | 5 | 5 | 5 | 5 | 5 | 5 |
|   | 0.63 | — | 1 | — | 4 | 5 | 5 | 5 | 5 | 5 | — |
| 8 | 1.25 | — | — | 5 | 5 | 5 | 5 | 5 | 5 | 4 | 4 |
|   | 0.63 | 1 | — | 5 | 5 | 5 | 5 | 5 | 5 | 5 | 5 |
| 9 | 1.25 | 2 | 2 | — | 4 | 5 | 5 | 5 | 4 | 4 | — |
|   | 0.63 | 1 | 2 | — | 4 | 5 | 5 | 5 | — | — | — |
| 11 | 2.5 | — | — | 5 | 5 | 5 | 5 | 5 | 5 | 5 | 5 |
|    | 1.25 | 1 | 1 | 5 | — | 5 | 5 | 5 | 5 | 4 | — |
| 12 | 2.5 | 1 | 1 | 5 | 5 | 5 | 5 | 5 | 5 | 5 | 5 |
| 13 | 1.25 | — | — | 5 | 5 | 5 | 5 | 5 | 5 | 5 | 5 |
|    | 0.63 | — | 1 | 4 | 4 | 5 | — | 5 | 5 | 4 | — |
| 15 | 1.25 | — | — | 5 | 5 | 5 | 5 | 5 | 5 | 5 | 5 |
|    | 0.63 | 0 | 1 | — | — | 5 | 5 | 5 | 5 | 5 | — |
| 16 | 2.5 | — | 1 | 5 | — | 5 | 5 | 5 | 5 | 5 | — |
|    | 1.25 | 1 | 1 | 5 | — | 5 | 5 | 4 | 5 | 4 | — |
| 17 | 2.5 | — | 0 | 5 | 5 | 5 | 5 | 5 | 5 | 5 | 5 |
|    | 1.25 | — | 0 | 5 | — | 5 | 5 | — | 5 | 4 | — |
| 18 | 2.5 | 0 | — | 5 | 5 | 5 | 5 | 5 | 5 | 5 | 5 |
|    | 1.25 | 0 | 1 | — | — | 4 | 5 | 5 | 5 | 4 | — |
| 19 | 2.5 | — | — | 5 | 5 | 5 | 5 | 5 | 5 | 5 | 5 |
| A | 2.5 | 0 | 0 | 0 | 0 | 0 | 0 | 0 | 0 | 0 | 0 |
|   |     | 0 | 0 | 0 | 0 | 0 | 0 | 0 | 0 | 0 | 0 |

TEST EXAMPLE 5

Vats (33 cm×23 cm×11 cm) were filled with upland field soil, and the seeds of wheat, catchweed bedstraw, persian speedwell, common chickweed, common lambsquarters, pale smartweed, wild buckwheat and annual bluegrass were sowed therein to 1 to 2 cm depth. A designed amount of the test compound formulated in an emulsifiable concentrate according to Formulation Example 2 was diluted with water, and the dilution was sprayed onto the soil surface by means of a small hand sprayer at a spray volume of 10 liters per are. The test plants were further grown in a greenhouse for 27 days, and the herbicidal activity was examined. The results are shown in Table 8.

TABLE 8

| Compound No. | Dosage (g/are) | Wheat | Catchweed bedstraw | Persian speedwell | Common chickweed | common lambsquarters | Pale smartweed | Wild buckwheat | Annual bluegrass |
|---|---|---|---|---|---|---|---|---|---|
| 1 | 1.25 | 1 | 5 | 5 | 5 | 5 | 5 | 5 | 5 |
| 2 | 0.63 | 1 | 4 | 5 | 4 | 5 | 5 | 5 | — |
| 4 | 0.63 | — | 5 | 5 | 5 | 5 | 5 | 5 | 4 |
|   | 0.32 | 1 | 4 | 5 | — | 5 | 5 | 5 | — |
| 6 | 1.25 | 0 | 5 | 5 | 5 | 5 | 5 | 5 | 4 |
|   | 0.63 | 0 | 4 | 5 | 4 | 5 | 5 | 5 | — |
| 7 | 0.63 | 2 | 5 | 5 | 5 | 5 | 5 | 5 | 5 |
|   | 0.32 | 1 | 5 | 5 | 5 | 5 | 5 | 5 | — |
| 8 | 1.25 | 1 | 5 | 5 | 5 | 5 | 5 | 5 | 5 |
|   | 0.63 | 1 | 4 | 5 | 4 | 5 | 5 | 5 | — |
| 9 | 0.63 | 1 | 5 | 5 | 5 | 5 | 5 | 5 | 5 |
|   | 0.32 | 1 | 4 | 5 | 5 | 5 | 5 | 5 | — |
| 13 | 0.63 | — | 5 | 5 | 5 | 5 | 5 | 5 | 5 |
|    | 0.32 | 0 | 4 | 5 | 5 | 5 | 5 | 5 | — |

TABLE 8-continued

| Compound No. | Dosage (g/are) | Wheat | Catchweed bedstraw | Persian speedwell | Common chickweed | common lambsquarters | Pale smartweed | Wild buckwheat | Annual bluegrass |
|---|---|---|---|---|---|---|---|---|---|
| | | | | Herbicidal activity | | | | | |
| 14 | 1.25 | — | 5 | 5 | 4 | 5 | 5 | 5 | 4 |
| | 0.63 | 0 | 4 | 5 | — | 5 | 4 | 5 | 4 |
| 15 | 0.63 | — | 5 | 5 | 5 | 5 | 5 | 5 | 5 |
| | 0.32 | 0 | 4 | 5 | 5 | 5 | — | 5 | — |
| 17 | 1.25 | — | 5 | 5 | 5 | 5 | 5 | 5 | 5 |
| | 0.63 | 0 | — | 5 | 5 | 5 | 5 | 5 | — |
| A | 1.25 | 0 | 0 | 0 | 0 | 0 | 0 | 0 | 0 |
| | 0.63 | 0 | 0 | 0 | 0 | 0 | 0 | 0 | 0 |

TEST EXAMPLE 6

Vats (33 cm×23 cm×11 cm) were filled with upland field soil, and the seeds of corn, wheat, sugar beet, common cocklebur, velvetleaf, black nightshade, tall morningglory, common lambsquarters and green foxtail were sowed therein and cultivated for 18 days in a greenhouse. A designed amount of the test compound formulated in an emulsifiable concentrate according to Formulation Example 2 was diluted with water containing a spreading agent, and the dilution was sprayed over the foliage of the test plants by means of a small hand sprayer at a spray volume of 5 liters per are. The test plants were further grown in the greenhouse for 20 days, and the herbicidal activity was examined. At the time of the application, the test plants were generally at the 1 to 4 leaf stage and in 2 to 12 cm height, although growing stage of the test plants varied depending on their species. The results are shown in Table 9.

and the test plants were grown in a greenhouse. Six days (at that time barnyardgrass began to germinate) thereafter, a designed amount of the test compound formulated in an emulsifiable concentrate according to Formulation Examle 2 and diluted with water (10 ml) was applied to the pots by perfusion. The test plants were grown for further 20 days in the greenhouse, and the herbicidal actvity was examined. For two days from the application, water was leaked with a 3 cm depth per day. The results are shown in Table 10.

TABLE 10

| Compound No. | Dosage (g/are) | Rice plant | Barnyard grass | Broadleaved weed | Needle spikerush | Arrow head |
|---|---|---|---|---|---|---|
| | | | Herbicidal activity | | | |
| 6 | 1 | 2 | 5 | 5 | 5 | 5 |
| | 0.5 | 0 | — | 5 | 4 | 4 |
| 13 | 0.5 | — | 5 | 5 | 5 | 5 |
| | 0.25 | 0 | — | 5 | 4 | 4 |
| A | 1 | 0 | 0 | 1 | 0 | 0 |
| | 0.5 | 0 | 0 | 0 | 0 | 0 |
| | 0.25 | 0 | 0 | 0 | 0 | 0 |

TABLE 9

| Compound No. | Dosage (g/are) | Corn | Wheat | Sugar beet | Common-cocklebur | Velvetleaf | Black nightshade | Tall morningglory | Common lambsquarters | Green foxtail |
|---|---|---|---|---|---|---|---|---|---|---|
| | | | | | Herbicidal activity | | | | | |
| 4 | 0.3 | — | — | 4 | 4 | 5 | 5 | 5 | 5 | — |
| | 0.1 | 1 | 1 | 3 | 3 | 5 | 4 | 5 | 5 | — |
| 6 | 0.3 | — | — | 5 | 4 | 5 | 4 | 5 | 5 | 4 |
| | 0.1 | 1 | 1 | 5 | 4 | 4 | 4 | 5 | 4 | — |
| 7 | 0.1 | — | — | 5 | 5 | 5 | 5 | 5 | 5 | 4 |
| | 0.03 | 1 | 1 | 4 | 5 | 5 | 4 | 5 | 5 | — |
| 8 | 0.3 | 1 | 0 | 5 | 5 | 5 | 5 | 5 | 5 | — |
| | 0.1 | 0 | 0 | 4 | — | 5 | 4 | 5 | 5 | — |
| 9 | 0.3 | 1 | 0 | 5 | 5 | 5 | 5 | 5 | 5 | — |
| | 0.1 | 0 | 0 | 3 | — | 5 | 4 | 5 | 5 | — |
| 11 | 0.1 | 1 | 1 | 4 | 5 | 5 | 5 | 5 | 5 | — |
| 13 | 0.1 | 1 | 1 | 5 | 5 | 5 | 5 | 5 | 5 | 4 |
| | 0.03 | 0 | 0 | 5 | — | 4 | 4 | 4 | 5 | — |
| 14 | 0.1 | 1 | 1 | — | 4 | 5 | 5 | 5 | 5 | — |
| 15 | 0.1 | — | 1 | 5 | 4 | 5 | 5 | 5 | 5 | — |
| 16 | 0.1 | 1 | 1 | 5 | 5 | 5 | 5 | 5 | 5 | 4 |
| | 0.03 | 1 | 1 | 4 | 4 | 5 | 5 | 5 | — | — |
| 18 | 0.1 | — | — | 4 | 5 | 5 | 5 | 5 | 5 | 4 |
| | 0.03 | 1 | 0 | 3 | — | 5 | 4 | 5 | 5 | — |
| 19 | 0.1 | — | — | 5 | 5 | 5 | 5 | 5 | 5 | 4 |
| | 0.03 | 1 | 0 | 5 | 4 | 5 | 5 | 5 | 5 | — |
| A | 0.3 | 0 | 0 | 0 | 0 | 1 | 1 | 0 | 1 | 0 |
| | 0.1 | 0 | 0 | 0 | 0 | 0 | 0 | 0 | 0 | 0 |
| | 0.03 | 0 | 0 | 0 | 0 | 0 | 0 | 0 | 0 | 0 |

TEST EXAMPLE 7

Wagner's pots (1/5000 are) were filled with paddy field soil, and the seeds of barnyardgrass (*Echinichloa oryzicola*), broad-leaved weeds (i.e. common falsepimpernel, toothcup, waterwort) and the statoblast of needle spikerush were sowed in 1 to 2 cm depth. Water was poured therein to make a flooded condition. Buds of arrowhead were sowed in 1 to 2 cm depth, and rice seedlings of the 3-leaf stage were transplanted therein,

What is claimed is:
1. A compound of the formula:

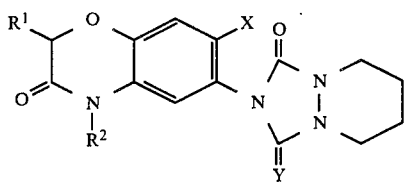

wherein R¹ is a hydrogen atom or a methyl group, R² is a C₁–C₅ alkyl group, a C₃–C₄ alkenyl group, a C₃–C₄ alkynyl group or a C₁–C₄ alkoxymethyl group, X is a hydrogen atom or a fluorine atom and Y is an oxygen atom or a sulfur atom.

2. The compound according to claim 1, wherein X is a fluorine atom.

3. The compound according to claim 2, wherein R¹ is a hydrogen atom or a methyl group and R² is a 2-propynyl group or a 2-propenyl group.

4. The compound according to claim 1, which is 2-[4-(2-propynyl)-7-fluoro-2H-1,4-benzoxazin-3(4H)-on-6-yl]hexahydro-1H-[1,2,4]-triazolo[1,2-a]pyridazine-1,3-dione.

5. The compound according to claim 1, which is 2-[4-(2-propynyl)-7-fluoro-2H-1,4-benzoxazin-3(4H)-on-6-yl]hexahydro-3-thioxo-1H-[1,2,4]-triazolo[1,2-a]pyridazin-1-one.

6. The compound according to claim 1, which is 2-[4-(2-propenyl)-7-fluoro-2H-1,4-benzoxazin-3(4H)-on-6-yl]hexahydro-1H-[1,2,4]-triazolo[1,2-a]pyridazine-1,3-dione.

7. The compound according to claim 1, which is 2-[4-(2-propenyl)-7-fluoro-2H-1,4-benzoxazin-3(4H)-on-6-yl]hexahydro-3-thioxo-1H-[1,2,4]-triazolo[1,2-a]pyridazin-1-one.

8. The compound according to claim 1, which is 2-[2-methyl-4-(2-propynyl)-7-fluoro-2H-1,4-benzoxazin-3(4H)-on-6-yl]hexahydro-1H-[1,2,4]-triazolo[1,2-a]pyridazine-1,3-dione.

9. A composition which comprises as an active ingredient a herbicidally effective amount of the compound according to claim 1, and an inert carrier or diluent.

10. A composition which comprises as an active ingredient a herbicidally effective amount of the compound according to claim 2, and an inert carrier or diluent.

11. A composition which comprises as an active ingredient a herbicidally effective amount of the compound according to claim 3, and an inert carrier or diluent.

12. A composition which comprises as an active ingredient a herbicidally effective amount of the compound according to claim 4, and an inert carrier or diluent.

13. A composition which comprises as an active ingredient a herbicidally effective amount of the compound according to claim 5, and an inert carrier or diluent.

14. A method for exterminating harmful weeds which comprises applying as an active ingredient a herbicidally effective amount of the compound according to claim 1 to the area where the weeds grow or will grow.

15. The method according to claim 14, wherein the application is effected in a field of corn, wheat, rice plant, soybean or cotton.

16. The method according to claim 15, wherein the application is effected in a field of wheat.

17. A method for exterminating harmful weeds which comprises applying as an active ingredient a herbicidally effective amount of the compound according to claim 2 to the area where the weeds grow or will grow.

18. A method for exterminating harmful weeds which comprises applying as an active ingredient a herbicidally effective amount of the compound according to claim 3 to the area where the weeds grow or will grow.

19. A method for exterminating harmful weeds which comprises applying as an active ingredient a herbicidally effective amount of the compound according to claim 4 to the area where the weeds grow or will grow.

20. A method for exterminating harmful weeds which comprises applying as an active ingredient a herbicidally effective amount of the compound according to claim 5 to the area where the weeds grow or will grow.

* * * * *